US012674182B2

(12) United States Patent
Tilly et al.

(10) Patent No.: US 12,674,182 B2
(45) Date of Patent: Jul. 7, 2026

(54) METHODS AND COMPOSITIONS FOR USE OF MITOCHONDRIAL THERAPIES TO IMPROVE FEMALE REPRODUCTIVE POTENTIAL

(71) Applicant: Northeastern University, Boston, MA (US)

(72) Inventors: Jonathan L. Tilly, Windham, NH (US); Dori Woods, Londonderry, NH (US)

(73) Assignee: Northeastern University, Boston, MA (US)

( * ) Notice: Subject to any disclaimer, the term of this patent is extended or adjusted under 35 U.S.C. 154(b) by 920 days.

(21) Appl. No.: 17/801,406

(22) PCT Filed: Feb. 22, 2021

(86) PCT No.: PCT/US2021/019062
§ 371 (c)(1),
(2) Date: Aug. 22, 2022

(87) PCT Pub. No.: WO2021/168419
PCT Pub. Date: Aug. 26, 2021

(65) Prior Publication Data
US 2023/0011622 A1     Jan. 12, 2023

Related U.S. Application Data

(60) Provisional application No. 62/979,177, filed on Feb. 20, 2020.

(51) Int. Cl.
| | |
|---|---|
| *C12N 15/873* | (2010.01) |
| *C12N 5/075* | (2010.01) |
| *G01N 33/50* | (2006.01) |

(52) U.S. Cl.
CPC ......... *C12N 15/873* (2013.01); *C12N 5/0609* (2013.01); *G01N 33/502* (2013.01)

(58) Field of Classification Search
None
See application file for complete search history.

(56) References Cited

U.S. PATENT DOCUMENTS

| | | | | |
|---|---|---|---|---|
| 8,647,869 | B2 | 2/2014 | Tilly et al. | |
| 9,845,482 | B2 * | 12/2017 | Tilly | A61P 15/08 |
| 2012/0315651 | A1 * | 12/2012 | Tilly | A61P 15/08 |
| | | | | 435/375 |
| 2013/0034527 | A1 | 2/2013 | Hyde et al. | |
| 2013/0059384 | A1 | 3/2013 | Tilly et al. | |

FOREIGN PATENT DOCUMENTS

| | | | | |
|---|---|---|---|---|
| WO | WO2012/142500 | * | 10/2012 | ............. G06Q 30/02 |
| WO | WO-2017/058900 A1 | | 4/2017 | |
| WO | WO-2017/117249 A1 | | 7/2017 | |
| WO | WO-2021/168419 A1 | | 8/2021 | |

OTHER PUBLICATIONS

Hoque et al., Journal of the Endocrine Society, 3: 324-339, published online Dec. 10, 2018 (Year: 2018).*
Hennet et al., Int. J. Dev. Biol. 56: 819-831 (2012) doi: 10.1387/ijdb.120133cc (Year: 2012).*
Parikh et al., Fertility and Sterility, 2006; 86: 839-847 (Year: 2006).*
Tzeng et al., "Mitochondria transfer (MIT) into oocyte from autologous cumulus granulosa cells (cGCs)", Fertility and Sterility 82 (2004): S53 (Year: 2004).*
Patra et al., J Nanobiotechnol (2018) 16:71 (Year: 2018).*
Cozzolino et al., "New Frontiers in IVF: mtDNA and autologous germline mitochondrial energy transfer." Reproductive Biology and Endocrinology 17(1) (2019): 55.
Extended European Search Report for EP Application No. 21756922.7 dated Mar. 20, 2024.
Fatum et al., "Levels of steroidogenic acute regulatory protein and mitochondrial membrane potential in granulosa cells of older poor-responder women." Fertility and sterility 91(1) (2009): 220-225.
Hua et al., "Effects of Granulosa Cell Mitochondria Transfer on the Early Development of Bovine Embryos In Vitro", Cloning and Stem Cells, vol. 9, No. 2, (2007), pp. 237-246.
Liu et al., "Age-related changes in the mitochondria of human mural granulosa cells." Human Reproduction 32(12) (2017): 2465-2473.
Urs et al., "Mitochondrial function in modulating human granulosa cell steroidogenesis and female fertility." International Journal of Molecular Sciences 21.10 (2020): 3592.
Desquiret-Dumas et al., "The mitochondrial DNA content of cumulus granulosa cells is linked to embryo quality," Human Reproduction, 32(3): 607-614 (2017).
Dumesic et al., "Cumulus Cell Mitochondrial Resistance to Stress in Vitro Predicts Oocyte Development During Assisted Reproduction," The Journal of Clinical Endocrinology & Metabolism, 101(5): 2235-2245 (2016).
International Search Report and Written Opinion for International Application No. PCT/US2021/019062 dated May 6, 2021.
MacDonald et al., "A method for freeze-fracture and scanning electron microscopy of isolated mitochondria," MethodsX, 5: 593-598 (2018).
MacDonald et al., "A nanoscale, multi-parametric flow cytometry based platform to study mitochondrial heterogeneity and mitochondrial DNA dynamics," Commun Biol, 2:258 (13 pages) (2019).

(Continued)

*Primary Examiner* — Christina M Borgeest
(74) *Attorney, Agent, or Firm* — Foley Hoag LLP; Dana M. Gordon; Mohanad Mossalam

(57) ABSTRACT

Disclosed are methods for increasing the fertilization rate of an oocyte in a granulosa cell-oocyte complex, and/or the success rate of in-vitro fertilization by using mitochondrial therapies. Also disclosed are methods of identifying compounds for fertility treatment.

19 Claims, 8 Drawing Sheets

(56)     References Cited

OTHER PUBLICATIONS

MacDonald et al., "New insights on mitochondrial heterogeneity observed in prepared mitochondrial samples following a method for freeze-fracture and scanning electron microscopy," Micron, 101: 25-21 (2017).
Taugourdeau et al., "The mitochondrial DNA content of cumulus cells may help predict embryo implantation," Journal of Assisted Reproduction and Genetics, 36: 223-228 (2019).

* cited by examiner

METHODS AND COMPOSITIONS FOR USE OF MITOCHONDRIAL THERAPIES TO IMPROVE FEMALE REPRODUCTIVE POTENTIAL

RELATED APPLICATION

This application is a National-stage application of International Application No. PCT/US21/19062, filed Feb. 22, 2021; which claims the benefit of priority to U.S. Provisional Patent Application Ser. No. 62/979,177, filed Feb. 20, 2020.

GOVERNMENT SUPPORT

This invention was made with government support under Grant Numbers AG012279 and HD091439 awarded by the National Institutes of Health, and Grant Number 1750996 awarded by the National Science Foundation. The government has certain rights in the invention.

BACKGROUND

The ovaries are the first organs to fail with age in almost all mammalian species, including humans, and this event is well out-of-sync with chronological lifespan. The decline in ovarian function is tightly associated with a decline in both the quantity and quality of oocytes available for ovulation and fertilization. While many mechanisms have been proposed as being responsible for driving the progressive deterioration of egg quality with age, more work is needed to increase the success rate of in-vitro fertilization. Hence, there is an urgent need to find new strategies to increase fertilization rates.

SUMMARY

Disclosed are methods for the early detection of pending ovarian aging (normal, due to chronological aging, as well as premature, due to disease conditions, genetic disorders, or exposure to agents or compounds that can impair female fertility), long before any other markers currently used for ovarian aging, deterioration of egg (oocyte) quality and compromised fertility in females become apparent. The invention also provides methods for improving natural and assisted reproduction in females, in particular in women whose egg and embryo quality have diminished due to maternal age. The invention also provides methods to improve the efficacy of in vitro (outside-the-body) systems designed to generate eggs from stem cells for reproductive purposes, such that higher quality egg quality can be achieved, which will translate into improved outcomes for fertilization and embryo development.

In one aspect, disclosed herein is a method of increasing the fertilization rate of an oocyte, wherein the oocyte is in a granulosa cell-oocyte complex, the method comprising transferring a composition of mitochondria into the granulosa cell, wherein the transferred mitochondria has a higher mitochondrial membrane potential (MMP) than the mitochondria in the granulosa cell. Numerous embodiments are further provided that can be applied to any aspect of the present invention described herein. For example, in some embodiments, the transferred mitochondrial is derived from an autologous or allogeneic cell. In some embodiments, the autologous or allogeneic cell is an autologous or allogeneic granulosa cell. In some embodiments, the autologous or allogeneic cell is an autologous or allogeneic cumulus cell.

In some embodiments, the transferred mitochondrial is derived from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the mitochondria is prepared using density gradient separation. In some embodiments, the mitochondria is prepared using differential centrifugation. In some embodiments, the mitochondria is prepared using flow cytometry. In some embodiments, the composition of mitochondria comprises at least 50%, at least 70%, or least 90% mitochondria with higher mitochondrial membrane potential (MMP) than the mitochondria in the granulosa cell. In some embodiments, the mitochondria is transferred ex vivo. In some embodiments, the mitochondria is transferred in vivo. In some embodiments, the mitochondria is transferred in vitro. In some embodiments, the mitochondria is transferred by vesicle-mediated transfer. In some embodiments, the mitochondria is transferred by incubating the autologous or allogeneic cell with the granulosa cell-oocyte complex. In some embodiments, the composition of mitochondria comprises at least 500 mitochondria, at least 2,500 mitochondria, or at least 5,000 mitochondria. In some embodiments, the oocyte is from a human subject.

In another aspect, disclosed herein is a method of identifying a compound for fertility treatment, comprising (a) contacting the compound and a granulosa cell; wherein the granulosa cell is in a granulosa cell-oocyte complex; (b) measuring the mitochondrial membrane potential (MMP) of the granulosa cell; and (c) detecting an increase in the MMP compared to an untreated granulosa cell, thereby identifying the compound for fertility treatment.

In another aspect, disclosed herein is a method of in vitro fertilization, the method comprising incubating a composition of mitochondria with a granulosa cell, wherein the granulosa cell is in a granulosa cell-oocyte complex; and fertilizing the oocyte in vitro to form a zygote, wherein and the incubated mitochondria has a higher mitochondrial membrane potential (MMP) than the mitochondria in the granulosa cell. Numerous embodiments are further provided that can be applied to any aspect of the present invention described herein. For example, in some embodiments, the incubated mitochondrial is derived from an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the incubated mitochondrial is derived from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the mitochondria is prepared using density gradient separation. In some embodiments, the mitochondria is prepared using differential centrifugation. In some embodiments, the mitochondria is prepared using flow cytometry. In some embodiments, the composition of mitochondria comprises at least 50%, at least 70%, or least 90% mitochondria with higher mitochondrial membrane potential (MMP) than the mitochondria in the granulosa cell. In some embodiments, the mitochondria is transferred to the granulosa cell ex vivo. In some embodiments, the mitochondria is transferred to the granulosa cell in vivo. In some embodiments, the mitochondria is transferred to the granulosa cell in vitro. In some embodiments, the mitochondria is transferred to the granulosa cell by vesicle-mediated transfer. In some embodiments, the mitochondria is transferred to the granulosa cell by incubating the autologous or allogeneic cell with the granulosa cell-oocyte complex. In some embodiments, the composition of mitochondria comprises at least 500 mitochondria, at least 2,500 mitochondria, or at least 5,000 mitochondria. In some embodiments, the oocyte is from a human subject.

In another aspect, disclosed herein is a method to promote the growth and maturation of a follicle or an immature oocyte, the method comprising: incubating a composition of mitochondria with a granulosa cell, wherein the incubated mitochondria has a higher mitochondrial membrane potential (MMP) than the mitochondria in the granulosa cell; and contacting the granulosa cell with mammalian ovarian tissue, wherein the mammalian ovarian tissue comprises at least one of the follicle and the immature oocyte, and wherein the granulosa cell promotes the growth and maturation of at least one of the follicle and the immature oocyte. Numerous embodiments are further provided that can be applied to any aspect of the present invention described herein. For example, in some embodiments, the incubated mitochondrial is derived from an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the mitochondria is prepared using density gradient separation. In some embodiments, the mitochondria is prepared using differential centrifugation. In some embodiments, the mitochondria is prepared using flow cytometry. In some embodiments, the composition of mitochondria comprises at least 50%, at least 70%, or least 90% mitochondria with higher mitochondrial membrane potential (MMP) than the mitochondria in the granulosa cell. In some embodiments, the mitochondria is transferred to the granulosa cell by vesicle-mediated transfer. In some embodiments, the mitochondria is transferred to the granulosa cell by incubating the autologous or allogeneic cell with the granulosa cell-oocyte complex. In some embodiments, the composition of mitochondria comprises at least 500 mitochondria, at least 2,500 mitochondria, or at least 5,000 mitochondria. In some embodiments, the mammalian ovarian tissue is from a human subject.

In one aspect, disclosed herein is a method to improve ex vivo generation of a functional oocyte, the method comprising: incubating a composition of mitochondria with a granulosa cell, wherein the incubated mitochondria has a higher mitochondrial membrane potential (MMP) than the mitochondria in the granulosa cell; and contacting the granulosa cell with an oocyte, wherein the oocyte is differentiated from a stem or progenitor cell. Numerous embodiments are further provided that can be applied to any aspect of the present invention described herein. For example, in some embodiments, the incubated mitochondrial is derived from an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the mitochondria is prepared using density gradient separation. In some embodiments, the mitochondria is prepared using differential centrifugation. In some embodiments, the mitochondria is prepared using flow cytometry. In some embodiments, the composition of mitochondria comprises at least 50%, at least 70%, or least 90% mitochondria with higher mitochondrial membrane potential (MMP) than the mitochondria in the granulosa cell. In some embodiments, the mitochondria is transferred to the granulosa cell by vesicle-mediated transfer. In some embodiments, the mitochondria is transferred to the granulosa cell by incubating the autologous or allogeneic cell with the granulosa cell-oocyte complex. In some embodiments, the composition of mitochondria comprises at least 500 mitochondria, at least 2,500 mitochondria, or at least 5,000 mitochondria. In some embodiments, the mammalian ovarian tissue is from a human subject.

In one aspect, provided herein is a method of increasing the fertilization rate of an oocyte, wherein the oocyte is in a granulosa cell-oocyte complex, the method comprising incubating a cell with the granulosa cell, wherein the cell comprises mitochondria with a higher mitochondrial membrane potential (MMP) than the mitochondria in the granulosa cell. Numerous embodiments are further provided that can be applied to any aspect of the present invention described herein. For example, in some embodiments, the cell is an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the cell is differentiated from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the oocyte is from a human subject.

In one aspect, provided herein is a method of in vitro fertilization, the method comprising incubating a cell with a granulosa cell, wherein the granulosa cell is in a granulosa cell-oocyte complex; and fertilizing the oocyte in vitro to form a zygote, wherein the cell comprises mitochondria with a higher mitochondrial membrane potential (MMP) than the mitochondria in the granulosa cell. Numerous embodiments are further provided that can be applied to any aspect of the present invention described herein. For example, in some embodiments, the cell is an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the cell is differentiated from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the oocyte is from a human subject.

In one aspect, provided herein is a method to promote the growth and maturation of a follicle or an immature oocyte, the method comprising: incubating a cell with a granulosa cell, wherein the cell comprises mitochondria with a higher mitochondrial membrane potential (MMP) than the mitochondria in the granulosa cell; and contacting the granulosa cell with mammalian ovarian tissue, wherein the mammalian ovarian tissue comprises at least one of the follicle and the immature oocyte, and wherein the granulosa cell promotes the growth and maturation of at least one of the follicle and the immature oocyte. Numerous embodiments are further provided that can be applied to any aspect of the present invention described herein. For example, in some embodiments, the cell is an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the cell is differentiated from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the oocyte is from a human subject.

On aspect, provided herein is a method to improve ex vivo generation of a functional oocyte, the method comprising: incubating a cell with a granulosa cell, wherein the cell comprises mitochondria with a higher mitochondrial membrane potential (MMP) than the mitochondria in the granulosa cell; and contacting the granulosa cell with an oocyte, wherein the oocyte is differentiated from a stem or progenitor cell. Numerous embodiments are further provided that can be applied to any aspect of the present invention described herein. For example, in some embodiments, the cell is an autologous or allogeneic cell. In some embodiments, the autologous or allogeneic cell is an autologous or allogeneic granulosa cell. In some embodiments, the autologous or allogeneic cell is an autologous or allogeneic cumulus cell. In some embodiments, the cell is differentiated from a stem cell or a progenitor cell. In some embodiments, the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell. In some embodiments, the oocyte is from a human subject.

In one aspect, provided herein is a method of identifying a granulosa cell-oocyte complex for fertilization, the method comprising measuring the mitochondrial membrane potential (MMP) of the granulosa cell; and identifying a granulosa cell-oocyte complex with a granulosa cell comprising a majority of mitochondria with a high MMP, thereby identifying the granulosa cell-oocyte complex for fertilization.

BRIEF DESCRIPTION OF THE DRAWINGS

FIG. 1A shows that mitochondria can be isolated based on size (small versus large,), and that size and $\Delta\psi$m are positively associated. FIG. 1B shows that mitochondria isolated by fluorescence-activated mitochondrial sorting (FAMS) retain full functional capacity to generate ATP from ADP substrate (small mitochondria exhibit low $\Delta\psi$m; large mitochondria exhibit high $\Delta\psi$m); FCCP is electron transport chain uncoupler.

FIG. 5A shows mitochondria isolated from donor cells are cultured with recipient cells resulting in rapid uptake of mitochondria (by 4 hours). Fluorescent microscopic images of recipient cells following overnight co-culture with donor mitochondria labeled to fluoresce red with MitoTracker CMXROS. FIG. 5B shows prior to transfer, the mitochondrial pellet was rinsed post-staining with MitoTracker CMXROS, and the wash was added to control cells to rule out artificial uptake of dye by recipient mitochondria; scale bar represents 100 μm. Images depict DAPI, MitoTracker-Red CMXROS and an overlay of the two respectively from left to right. FIG. 5C shows mitochondrial depleted cells collected at Day 1 and Day 14 following an overnight donor mitochondrial transfer mtDNA full difference against nuclear DNA. N=3; p=0.02257. FIG. 5D shows donor and recipient cell mtDNA full difference against nuclear DNA; n=4; p=0.01013. FIG. 5E shows depleted recipient cells collected after an overnight mitochondrial transfer consisting of differing mitochondria inputted (23 μg, 11.5 μg, 3.85 μg, 0 μg) mtDNA full difference against nuclear DNA; n=3; p=0.000164. FIG. 5F shows depleted recipient cells collected after an overnight mitochondrial transfer consisting of differing mitochondria inputted (23 μg, 11.5 μg, 3.85 μg, 0 μg) mtDNA full difference against nuclear DNA; n=3; p=0.000126. FIG. 5G shows SNP identification of sequenced mtDNA for the donor cell line, the depleted recipient cell line with donor transferred mitochondria (depleted recipient+donor mito), and donor cell line (top to bottom, respectively).

FIG. 6A shows that 25.1% of events within the pre-determined size gate (0.22-2 μm) in the cumulus cell overnight culture media sample displayed positive fluorescence for MitoTracker Green FM, while only 16.4% of events within the same size gate displayed positive fluorescence in the cumulus-oocyte complex overnight culture spent media sample. FIG. 6B shows that JC-1 aggregate fluorescence, measured in the PE-A channel via FAMS (MacDonald et al., *Communications Biology* 2019 Jul. 11; 2:258), is indicative of high-mitochondrial membrane potential; which is classically used as a measure of mitochondrial respiratory activity. FIG. 6C shows that cumulus granulosa cell mitochondria obtained from culture media can be stratified based on size, as determined by side scatter (SSC) and forward scatter (FSC).

DETAILED DESCRIPTION

Figure 1A:
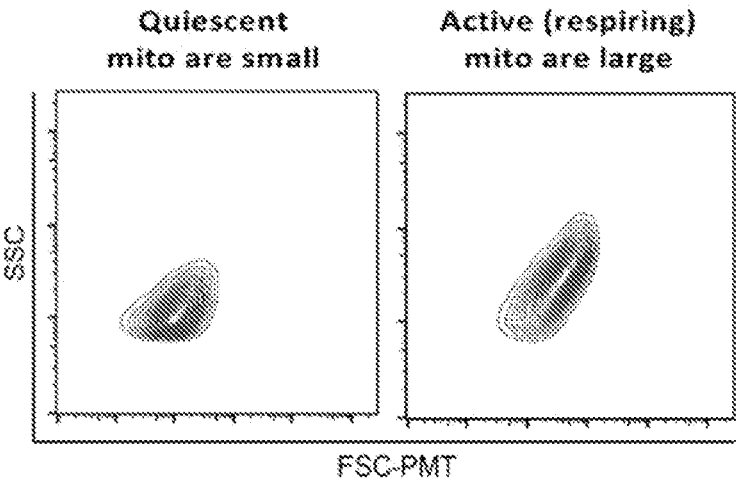
FIGS. 1A-1B show properties of mitochondria (MMP or $\Delta\psi$m) assessed by a flow cytometry platform.

The ability of the female germ cell—hereafter referred to as the oocyte—to mature into an egg, fertilize and develop into a healthy preimplantation embryo required for successful pregnancy, whether fertilization occurs inside (in vivo) or outside (in vitro) the body, is influenced by the quality of the oocyte itself (viz. intrinsic factors) as well as oocyte-extrinsic factors deriving from the environment in which the oocyte resides. One of the most critical extrinsic factors affecting oocyte viability and developmental competency are the somatic granulosa cells (GCs). These specialized cells are found adjacent to, and in direct physical contact with, the oocyte (Forming GC-oocyte complex) throughout its developmental journey inside of the ovaries and all the way to the point of fertilization outside of the ovaries. Changes in these factors as a consequence of normal chronological aging, disease conditions or a variety of insults, including, but not limited to, chemotherapy, radiotherapy and exposure to biohazardous environmental chemicals, can negatively impact on oocyte quality, leading to failed fertilization, failed embryonic development, failed implantation of the embryo into the lining of the uterus to establish a pregnancy, or failed maintenance of a pregnancy (viz. miscarriage).

The ovaries are the first organs to fail with age in almost all mammalian species, including humans, and this event is well out-of-sync with chronological lifespan. For example, while the average lifespan of women in the United States of America approaches 80 years, ovarian function begins a precipitous decline around 35-38 years of age. In the context of reproductive potential, women are considered at advanced maternal age by 38 years, long before the average age of menopause (complete loss of reproductive potential) around age 51 and certainly well before the average age of death. The decline in ovarian function is tightly associated with a decline in both the quantity and quality of oocytes available for ovulation and fertilization. While many mechanisms have been proposed as being responsible for driving the progressive deterioration of egg quality with age, mitochondrial dysfunction appears central to the process. For example, there is a marked decrease in mitochondrial number and function in oocytes with age, and this is associated with abnormal mitochondrial distribution patterns. These intrinsic changes in oocytes that negatively impact fertilization and developmental competency have been the impetus for development and clinical testing of new therapeutic approaches involving microinjection of high-quality mitochondria directly into oocytes at the time of fertilization to improve in-vitro fertilization (IVF) success rates. It is important to emphasize that all of this work focusses on direct targeting of the oocyte to improve its function.

Notably, the decline in oocyte quantity with age coincides with a dramatic decrease in the number of GCs that surround and support the oocyte as the oocyte develops. These highly specialized cells participate in bi-directional communication with the oocyte, and also produce a number of hormones important for the health in women, including estrogen (E2). Not surprisingly, many hallmarks of reproductive aging in women are those that are measurable based on a decline in GC numbers or function, including decreased production of anti-Müllerian hormone (AMH; produced by less mature GCs) and E2 (produced by more mature GCs), and elevated levels of circulating follicle-stimulating hormone (FSH), which occurs as a result of reduced inhibin production by GCs with age. These well-established clinical endpoints have long solidified the value of using changes in GC hormone production as markers of female reproductive aging, but all of these changes occur as a consequence of ovarian aging. Predictive or diagnostic markers of pending ovarian aging do not exist.

It is also important to emphasize that GCs have been reported to impact on the decline in oocyte quality with age as well. For example, removing GCs from GC-oocyte complexes retrieved from female mice for ex-vivo study significantly reduces the incidence of oocyte death via apoptosis, essentially resulting in oocytes with a "youthful" phenotype. Additionally, removal of GCs from oocytes of reproductively aged female mice in vitro results in greater rates of preimplantation embryo (viz. blastocyst) formation following IVF, and that exposure of GC-oocyte complexes to FSH (which specifically targets GCs in the ovary and is elevated with age) negatively impacts on the rate of blastocyst development following IVF. Our own studies have further demonstrated that removal of the GCs from GC-oocyte complexes containing immature oocytes matured in vitro abolishes the elevated rates of aneuploidy seen in oocytes with advancing maternal age. All of these findings point to a role for GCs in negatively impacting oocyte quality as the ovaries age; however, the identity of the potential changes in GCs that lead to decreased viability or function of the adjacent oocyte are not known.

Figure 2:
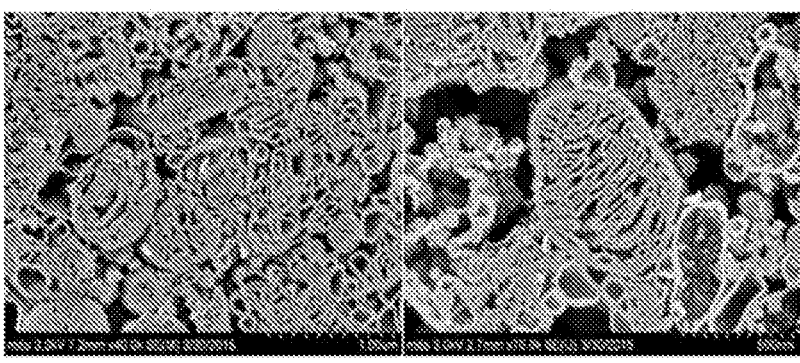
FIG. 2 shows that mitochondria isolated by FAMS retain normal ultrastructural features.
Figure 3:
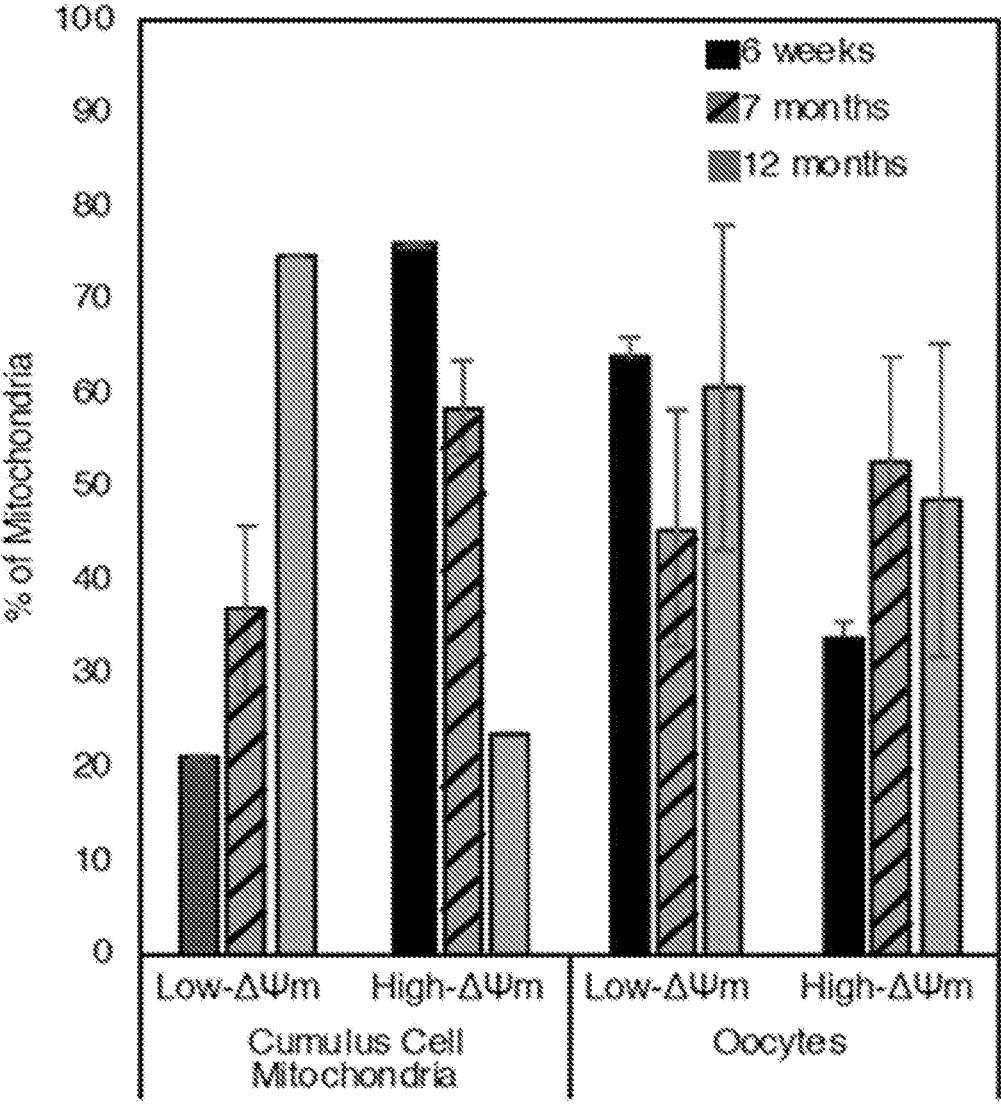
FIG. 3 shows mitochondrial membrane potential dissipates in GCs with age. While $\Delta\Psi$m is relatively unchanged in oocytes with age, GCs exhibit dissipated $\Delta\Psi$m by 7-months that worsens much further by 12 months of age, when oocyte quality has severely deteriorated and the females exhibit fertility issues due to maternal aging.
Figure 4:
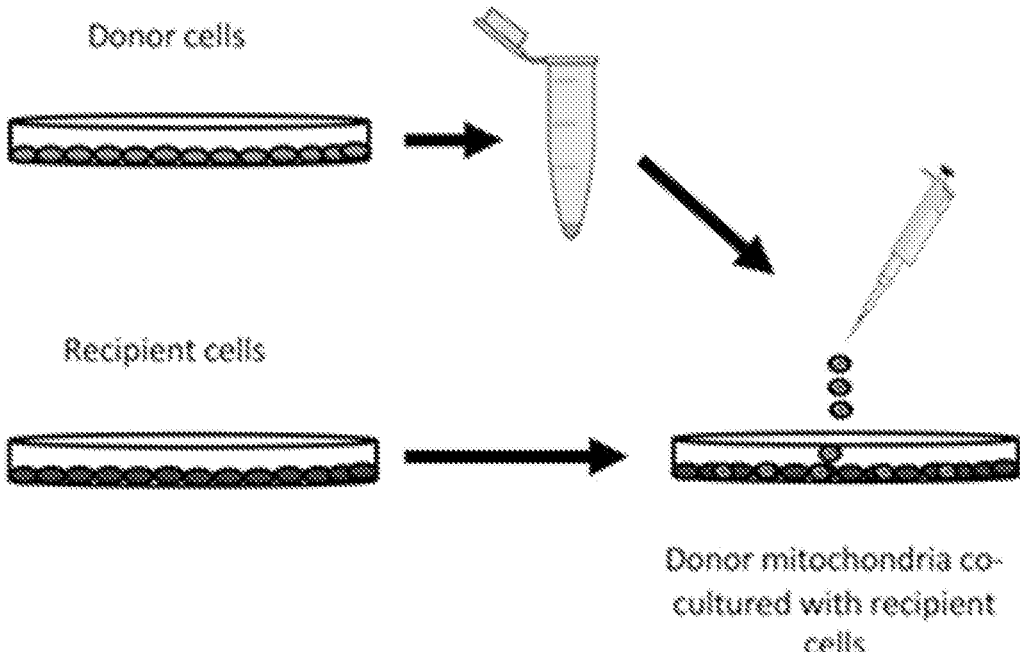
FIG. 4 shows mitochondrial transfer (transplantation) methodology. Mitochondria isolated from donor cells are cultured with recipient cells, resulting in rapid uptake (by 4 hours) through a mechanism involving actin-mediated endocytosis and micropinocytosis.

In our studies focused on mapping changes in mitochondrial dynamics in oocytes with age, we serendipitously made the observation that the GCs proximal to the oocytes under investigation exhibited changes in mitochondrial membrane potential (MMP), a key endpoint associated with mitochondrial activity and bioenergetic function, long before any changes in oocyte mitochondria occur. Past studies have shown that high MMP is a hallmark feature of healthy mitochondria, by virtue of the fact that the generation of cellular energy in the form of ATP by mitochondria in all cells is tied to maintenance of a high MMP. Conversely, a low MMP is associated with a very low level of, or no, mitochondrial respiration (viz. oxidative phosphorylation through the electron transport chain in the mitochondrial matrix), or defective mitochondrial respiration which generates elevated levels of reactive oxygen species (ROS) that can cause widespread macromolecular damage to proteins, lipids and nucleic acids. By combining a highly-sensitive flow cytometry platform termed fluorescence-activated mitochondrial sorting or FAMS (FIGS. 1 and 2), with mitochondrial membrane activity-specific dyes that exhibit different fluorescent spectra depending on whether the MMP is low or high (FIG. 1), we have identified the early occurrence of a highly reproducible and quantifiable shift in numbers of mitochondria in GCs that exhibit high versus low MMP (FIG. 3). These changes in the somatic cells surrounding the oocyte are first detectable approximately halfway through the normal reproductive lifespan long before oocyte quality becomes compromised, in the absence of any parallel changes in MMP in mitochondria of oocytes at the same age point. Specifically, GCs of GC-oocyte complexes collected from adult females very early in reproductive life contain mitochondria that are 80% or more of the high MMP type. By mid-reproductive life, a clear increase in the proportion of GC mitochondria with a low MMP is observed, and this shift towards more mitochondria with a low MMP becomes progressively more prominent in females towards late reproductive life; for the latter, the population of mitochondria in GCs becomes 80% or more those with a low MMP (FIG. 3). That we can detect significant changes in MMP in mitochondria of GCs well before any other signs of pending reproductive compromise in females, and that these changes are indicative of aberrant mitochondrial function in the somatic cells that are required for proper oocyte development, maturation and fertilization, support the novel utility of GC mitochondria for both diagnostic and therapeutic applications in natural and assisted reproduction in female mammals (FIGS. 4 and 5).

The present invention is based, in part, on our unexpected findings that dissipation of mitochondrial membrane potential (MMP) can be detected in GCs of adult mammalian ovaries long before any other known markers of compromised oocyte quality and fertility associated with ovarian aging. Such dissipation has been experimentally tied to aberrant mitochondrial function, including abnormal bioenergetic capacity and excessive generation of ROS, which, if left unchecked or unremedied, could lead to improper signaling between GCs and their adjacent oocytes as well as to disruptions in oocyte function tied to fertilization and developmental competency.

Disclosed herein is also an additional parameter regarding the mitochondrial readout and potential acquisition of mitochondria from cumulus granulosa cells. Cumulus granulosa cells spontaneously release mitochondria into cell culture media following a short-term culture period, and these mitochondria have modified membrane potential depending on our experimental conditions. Therefore, this solidifies mitochondrial membrane potential as one readout for the invention, and further adds that we potentially do not even need to harvest cells to obtain mitochondria from granulosa cumulus cells. Furthermore, examination of these mitochondria also reveals differences in mitochondrial size, which could be another parameter for gauging the quality of mitochondria from cumulus cells.

Isolated, functional mitochondria could be introduced to cell culture, leading to internalization by live cells, through an actin-dependent mechanism, most likely micropinocytosis, although exact mechanisms are still debated. This process was originally termed "mitochondrial transformation," but as its therapeutic potential was revealed, it has been more commonly referred to as "mitochondrial transplantation." This phenomenon has been demonstrated to function across cell types, as well as with both autologous and non-autologous mitochondria. Mitochondrial transplants are as both a potent therapeutic and an attractive experimental tool.

To effectively replace the mitochondrial population from one cell line with that of another, a protocol designed to deplete cells of physical mitochondria through enforced mitophagy is followed [See Correia-Mello et al. 2017] and utilized these depleted cells in tandem with mitochondrial transplantation.

In one aspect, the invention provides a method of diagnosing or detecting pending problems with fertility in female mammals due to the deterioration of oocyte quality associated with chronological aging, genetic disorders, disease conditions or exposure to various chemicals or agents capable of causing reproductive harm in females. The method comprises collection of GCs from individual ovarian follicles in vivo, through any number of conventional means including, but not limited to, ultrasound-guided transvaginal needle aspiration, and assessment of the mitochondrial profiles in the collected GCs for changes in mitochondrial dynamics indicative of aberrant function.

In some embodiments, the changes in GC mitochondrial dynamics with age are reflected by changes in the proportion of mitochondria with a high versus low MMP.

In yet other embodiments, the changes in GC mitochondrial dynamics, as reflected by changes in the proportion of mitochondria with a high versus low MMP, are caused by factors other than chronological aging that can prematurely compromise female fertile potential, including, but not limited to, disease conditions, genetic disorders, chemotherapy, radiotherapy, tobacco use, and exposure to environmental chemicals or agents.

In another aspect, the invention provides a method of selecting the best GC-oocyte complex for use in assisted reproduction. The method comprises analysis of some GCs from each GC-oocyte complex for mitochondrial profiles, most notably shifts in the proportion of mitochondria with a high versus low MMP, which would be predictive of better quality (GCs with mitochondria mostly comprised of the high MMP type) or poorer quality (GCs with mitochondria comprised mostly of the low MMP type) oocytes for fertilization, preimplantation embryogenesis and pregnancy success.

In some embodiments, the method based on the assessment of MMP status in GCs is used to select those oocytes with the greatest chance of supporting pregnancy success prior to the fertilization of the oocyte.

In yet another aspect, the invention provides a method of improving the outcomes of natural and assisted reproduction in females. The method comprises collection of mitochondria with a high MMP and the subsequent transfer of these mitochondria to GCs of GC-oocyte complexes to improve oocyte fertilization, preimplantation embryogenesis, and pregnancy success in female subjects.

In one embodiment, the mitochondria with a high MMP are isolated from cells autologous to the female subject in need of fertility assistance, most preferably from GCs autologous to the female subject in need of fertility assistance.

In another embodiment, the mitochondria with a high MMP are isolated from cells that can give rise to GCs.

In yet another embodiment, the mitochondria with a high MMP are isolated by any number of means, including differential centrifugation, density gradient centrifugation and flow cytometry, for subsequent use as a diagnostic or therapeutic.

In a different aspect, the invention provides a method for assessing the potential efficacy of a therapeutic compound or agent designed to improve, enhance or restore female fertility. The method comprises exposure of a female subject (in vivo), or exposure of GC-oocyte complexes from a female subject (in vitro), to a compound or agent of choice, which is then followed by assessment of the impact of that compound or agent on mitochondrial profiles, in particular the proportion of mitochondria with high versus low MMP types, in GCs.

In yet another aspect, the invention provides a method of improving the success rates of ex-vivo generation of functional oocytes from stem or progenitor cells. The method comprises exposure of stem or progenitor cells used for gametogenesis to cells with mitochondria with a high MMP.

In one embodiment, the cells with mitochondria with a high MMP are GCs.

In another embodiment, the exposure to cells with mitochondria with a high MMP occurs with the stem or progenitor cells prior to oogenesis, whereas in a different embodiment the exposure to cells with mitochondria with a high MMP occurs with oocytes or GC-oocyte complexes formed from the stem or progenitor cells.

In another aspect, the invention provides a method of improving the success rates of ex-vivo generation of functional oocytes from stem or progenitor cells. The method comprises exposure of stem or progenitor cells used for gametogenesis to mitochondria with a high MMP.

In one embodiment, the cells from which mitochondria with a high MMP are derived are GCs.

In another embodiment, the exposure to mitochondria with a high MMP occurs with the stem or progenitor cells prior to oogenesis, whereas in a different embodiment the exposure to mitochondria with a high MMP occurs in GC-oocyte complexes formed from the stem or progenitor cells.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

As used herein, the singular forms "a," "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the "administration" of an agent, drug, compound, mitochondria, or cells to a subject includes any route of introducing or delivering to a subject an agent, drug, compound, or cells to perform its intended function. Administration can be carried out by any suitable route, including, e.g., localized injection (e.g., catheter administration or direct intra-ovarian injection), systemic injection, intravenous injection, intrauterine injection, orally, intranasally, and parenteral administration. Administration includes self-administration and the administration by another.

As used herein, "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell or granulosa cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). Oocytes are an example of a terminally differentiated cell type.

As used herein, the term "enriched population" refers to a purified or semi-purified population of granulosa cells or granulosa cell precursors. In some embodiments, a specific population of granulosa cells or granulosa cell precursors is enriched by sorting the granulosa cells or granulosa cell precursors from the population of differentiating multi-potent cells, e.g., by fluorescence activated cell sorting (FACS), magnetic assisted cell sorting (MACS), or other cell purification strategies known in the art for separation of a specific populations of cells from a general population of cells. By way of example, but not by limitation, in some embodiments, an enriched population of granulosa cells or granulosa cell precursors is a purified or semi-purified population of granulosa cells or granulosa cell precursors that have been isolated from differentiating multi-potent cells by FACS.

As used herein, the term "effective amount" or "therapeutically effective amount" refers to a quantity sufficient to achieve a desired effect, e.g., an amount of granulosa cells with high MMP that will elevate steroidal hormone levels in a subject in need thereof. By way of example, but not by limitation, in some embodiments, a therapeutically effective amount of granulosa cells is the amount of granulosa cells necessary to raise a subject's steroidal level as compared to a normal subject's steroidal hormone level. In the context of hormone therapy applications, in some embodiments, the amount of granulosa cells or granulosa cell precursors administered to the subject will depend on the condition or disease state of the subject, e.g., a menopause subject or subject who has had a hysterectomy, and on the characteristics of the subject, such as general health, age, sex, body weight and tolerance to drugs. The skilled artisan will be able to determine appropriate dosages depending on these and other factors.

As used herein, a "follicle" refers to an ovarian structure consisting of a single oocyte surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase.

As used herein, the term "immature oocyte" refers to primary oocytes that are arrested in prophase I.

As used herein, the term "mature follicle" refers to a follicle that has actively proliferating granulosa cells surrounding a developing oocyte that responds to exogenous hormones. By way of example, but not by limitation, mature or maturing follicles increase in size due to proliferation of the granulosa cells, expansion of the oocyte following resumption of meiosis, and because of the development of a fluid filled antrum.

As used herein, the term "mature oocyte" refers to an oocyte arrested in metaphase II of meiosis capable of fertilization following sperm penetration or activation of parthenogenesis by addition of calcium ionophore.

As used herein, the term "stimulating agent" refers to any compound, hormone, peptide, drug, or other agent that stimulates granulosa cells or granulosa cell precursors to secreted steroidal hormones, e.g., estradiol or progesterone. By way for example, but not by limitation, in some embodiments, stimulating agents include but are not limited to follicle stimulating hormone (FSH) and 8-Bromoadenosine 3',5'-cyclic monophosphate (8-br-cAMP).

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

The term "comprise" is generally used in the sense of include, that is to say permitting the presence of one or more features or components. Wherever embodiments, are described herein with the language "comprising," otherwise analogous embodiments described in terms of "consisting of," and/or "consisting essentially of" are also provided.

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" can also mean increase female reproductive potential.

The term "preventing" is art-recognized, and when used in relation to a condition, such as infertility, a local recurrence (e.g., pain), a disease such as a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of infertility includes, for example, reducing the number of GCs with low MMP and/or increasing the number of GCs with high MMP in a population of patients receiving a prophylactic treatment relative to an untreated control population, and/or delaying the appearance of GCs with low MMP in a treated population versus an untreated control population, e.g., by a statistically and/or clinically significant amount.

As used herein, the term "functional mitochondria" refers to mitochondria that produce ATP and can be used interchangeably with the term "respiring mitochondria."

The term "autologous" as used herein refers to biological compositions obtained from the same subject.

The term "allogeneic" as used herein refers to biological compositions obtained from a different subject.

As used herein "an increase in ATP generation or production" refers to an amount of ATP production that is at least about 1-fold more than (for example 1, 2, 3, 4, 5, 6, 7, 8, 9, 10, 20, 30, 40, 50, 60, 70, 80, 90, 100, 1000, 10,000-fold or more) the amount of ATP production in a reference level, as that term is defined herein. ATP production can be measured by standard methods known in the art.

As used herein, "high ATP-generating capacity mitochondria" refers to mitochondria having a high mitochondrial membrane potential, as determined by a probe which can distinguish between high and low (or between high and medium/low) membrane potential. One method of identifying mitochondria with high mitochondrial membrane potential is the use of the fluorescent probe 5,5',6,6'-tetrachloro-1,1',3,3'-tetraethylbenzimidazolyl carbocyanine iodide (JC-1, Invitrogen T3168, Life Technologies Corp., Carlsbad, CA), which fluoresces red-orange (590 nm) in high quality mitochondria but fluoresces green (510-520 nm) in medium and/or low quality mitochondria. (See, e.g., Garner et al., Bio. Reprod. 1997 57:1401-1406; Reers et al, Biochemistry 1991 30:4480-4486; Cossariza et al, Biochem Biophys Res Commun 1993 197:40-45; Smiley et al., Proc Natl Acad Sci USA 1991 88:3671-3675).

The term "ex-vivo method" as used herein refers to any method comprising steps performed exclusively outside the human body. The term "enriching" as used herein refers to any action designed to increase the mitochondrial content, e.g. the number of intact mitochondria, of a human cell.

The term "induced pluripotent stem cells (iPSc)" as used herein refers to human pluripotent stem cell generated from adult cells.

The term "isolated human functional mitochondria" as used herein refers to intact mitochondria isolated from cells obtained from a subject not afflicted with a mitochondrial disease.

Methods for Isolating Granulosa Cells or Granulosa Cell Precursors from Multi-Potent Cells In some embodiments, the present technology relates to identifying and isolating granulosa cells or granulosa cell precursors from multi-potent cells.

In some embodiments, multi-potent cells are engineered to contain at least one granulosa cell specific gene reporter, wherein expression of the granulosa cell specific gene reporter is indicative of a cell that is a granulosa cell or a granulosa cell precursor.

Multi-potent cells include, but are not limited to, embryonic stem cells (ESCs), pluripotent stem cells, induced pluripotent stem cells (iPSCs) or otherwise reprogrammed somatic cells, bone marrow derived cells, peripheral blood-derived cells.

The multi-potent cells may be any mammalian multi-potent cell. Mammals from which the multi-potent cell can originate, include, for example, farm animals, such as sheep, pigs, cows, and horses; pet animals, such as dogs and cats;

laboratory animals, such as rats, mice, monkeys, and rabbits. In some embodiments, the mammal is a human.

In some embodiments, the granulosa cell specific reporter includes a fluorescent reporter under regulatory control of an ovarian granulosa cell-specific gene. Ovarian granulosa cell-specific genes include, but are not limited to, forkhead box L2 (Foxl2), wingless type MMTV integration site family, member 4 (WNT4), Nr5a1, Dax-1, ATP-binding cassette, subfamily 9 (Abca9), acetyl-Coenzyme A acyltransferase 2 (mitochondrial 3-oxoacyl-Coenzyme A thiolase; Acaa2), actin, alpha 2, smooth muscle, aorta (Acta2), a disintegrin-like and metallopeptidase (reprolysin-like) with thrombosin type 1 motif, 17 (Adamts17), ADAMTS-like 2 (Adamtsl2), AF4/FMR2 family, member 1 (Aff1), expressed sequence AI314831 (AI314831), Aldo-keto reductase family 1, member C14 (Akr1c14), aldo-keto reductase family 1, Notch2, and member C-like (Akr1cl). Fluorescent reporters include but are not limited to, *Discosoma* sp. red (DsRed), green fluorescent protein (GFP), yellow fluorescent protein (YFP), and orange fluorescent protein (OFP).

In some embodiments, the granulosa cell specific reporter is a non-fluorescent reporter under regulatory control of an ovarian granulosa cell-specific gene. Non-fluorescent reporters include, but are not limited to, luciferase and beta-galactosidase.

The granulosa cell specific reporter can be engineered by any methods known in the art. By way of example, but not by limitation, in some embodiments, a granulosa cell specific reporter is engineered by identifying a granulosa cell specific gene promoter, determining a conserved region of the gene promoter, isolating the conserved region from genomic DNA using PCR, and cloning the conserved region into a vector containing a fluorescent marker.

Engineering multi-potent cells to contain the granulosa cell specific gene reporter can be accomplished by any method known in the art. By way of example, but not by limitation, in some embodiments, the granulosa cell specific gene reporter is inserted into the multi-potent cells by using electroporation. Other methods for inserting the granulosa cell specific gene reporter include, but are not limited to, viral transduction, cationic liposomal transfection, multi-component lipid based transfection, calcium phosphate, DEAE-dextran, and direct delivery.

Multi-potent cells that contain the granulosa cell specific gene reporter can be selected for by any cell selection method known in the art. Examples of methods for cell selection include, but are not limited to, fluorescence activated cell sorting (FACS), differential adhesion, selection of precursor or progenitor cells for clonal expansion, and selection for antibiotic resistance.

Populations of multi-potent cells that contain the granulosa cell specific gene reporter are cultured under conditions suitable for differentiation of the mammalian multi-potent cells to granulosa cells or granulosa cell precursors. The multi-potent cells can be induced to differentiate by any methods commonly used in the art. By way of example, but not by limitations, undifferentiated ESCs containing granulosa cell specific gene reporter that are cultured on a mitotically-inactivated mouse embryonic fibroblast (MEF) feeder layer can be induced to differentiate by separating the ESCs from the MEF by differential adhesion and culturing the ESCs with 15% FBS in the absence of LIF on gelatin-coated plates in a monolayer. Other methods for differentiation include, but are not limited to, inducement by embryoid body formation in hanging droplets.

In some embodiments, growth factors or activators of signaling pathways for granulosa cell specification are used to direct multi-potent cell to differentiate into granulosa cells or granulosa cell precursors. Growth factors or activators of signaling pathways for granulosa cell specification, include, but are not limited to bFGF or activators of the Notch signaling pathway, e.g., Jagged1 or Jagged2.

After inducement of differentiation of the population of multi-potent cells, granulosa cells or granulosa cell precursors are identified and isolated. In some embodiments, the granulosa cells or granulosa cell precursors are identified by the expression of fluorescence under the control of the granulosa cell-specific gene. In some embodiments, the granulosa cells or granulosa cell precursors are isolated into enriched populations of granulosa cells or granulosa cell precursors by FACS, antibody-based immunomagnetic sorting (e.g., magnetic assisted cell sorting (MACS)), differential adhesion, clonal selection and expansion, or antibiotic resistance.

In some embodiments, the granulosa cells or granulosa cell precursors are isolated using a cell surface markers(s) selective for or specific to granulosa cells or granulosa cell precursors. Examples of cell surface markers selective for or specific to granulosa cells or granulosa cell precursors include, but are not limited to anti-mullarian hormone receptor, and Notch receptor (Notch2).

Methods for Growth and Maturation of Follicles and Immature Oocytes in Ovarian Tissue In one aspect, provided herein are methods method to promote the growth and maturation of a follicle or an immature oocyte, the method comprising:

incubating a composition of mitochondria with a granulosa cell, wherein the incubated mitochondria has a higher mitochondrial membrane potential (MMP) than the mitochondria in the granulosa cell; and contacting the granulosa cell with mammalian ovarian tissue, wherein the mammalian ovarian tissue comprises at least one of the follicle and the immature oocyte, and wherein the granulosa cell promotes the growth and maturation of at least one of the follicle and the immature oocyte.

U.S. Pat. No. 10,525,086 describes methods for growth and maturation. The patent is hereby incorporated by reference in its entirety.

In some embodiments, enriched populations of granulosa cells or granulosa cell precursors are used to promote the growth and maturation of follicles, follicle-like structures, and/or immature oocytes in ovarian tissue.

In some embodiments, ovarian tissue is contacted by an enriched population of granulosa cells or granulosa cell precursors wherein the granulosa cells or granulosa cell precursors promote the growth and maturation of follicles, follicle-like structures, and/or immature oocytes in ovarian tissue. In some embodiments, after contact with the ovarian tissue, the granulosa cells or granulosa cell precursors migrate to follicles, follicle-like structures, and/or immature oocytes or oocyte precursors in ovarian tissue to produce or enrich an ovarian somatic environment that induces maturation of follicles and immature oocytes.

In some embodiments, the ovarian tissue is contacted by an enriched population of granulosa cells or granulosa cell precursors in vivo. In some embodiments, in vivo administration includes, but is not limited to, localized injection (e.g., catheter administration or direct intra-ovarian injection), systemic injection, intravenous injection, intrauterine injection, and parenteral administration.

In some embodiments, the ovarian tissue is contacted by an enriched population of granulosa cells or granulosa cell precursors ex vivo. In some embodiments, ex vivo contact includes, but is not limited to, direct injection of ovarian tissue, aggregation with intact or dissociated ovarian tissue, and co-culture with ovarian tissue. In some embodiments, the contacted ex vivo ovarian tissue is cultured and then transplanted or implanted into a subject's ovaries or surrounding tissues. Methods for transplanting or implanting include, but are not limited to, engraftment onto ovary, injection or engraftment of tissue into ovary following ovarian incision, and engraftment into fallopian tube.

In some embodiments, the contacted ex vivo ovarian tissue is cultured and then frozen and stored after growth and maturation of the follicle and/or oocyte.

The ovarian tissue may be any mammalian ovarian tissue. Mammals from which the ovarian tissue can originate, include, for example, farm animals, such as sheep, pigs, cows, and horses; pet animals, such as dogs and cats; laboratory animals, such as rats, mice, monkeys, and rabbits. In some embodiments, the mammal is a human.

In some embodiments, the enriched population of granulosa cells or granulosa cell precursors and the ovarian tissue are autologous. In some embodiments, the enriched population of granulosa cells or granulosa cell precursors and the ovarian tissue are heterologous allogeneic.

In some embodiments, the promotion of growth and maturation of follicles, follicle-like structures, and/or immature oocytes or oocyte precursors in ovarian tissue by granulosa cells or granulosa cell precursors is measured by an increase in follicle diameter, increase in granulosa cell number, increase in steroid hormone production, increase in oocyte diameter, or a combination thereof.

The diameter of a maturing follicle or oocyte varies from species to species and is identifiable by one skilled in the art since mature follicle sizes for specific species is generally known in the art. By way of example, but not by limitation, in some embodiments, a follicular diameter of a human follicle that is indicative of a mature or maturing follicle is a diameter greater than about 30 μm. Alternatively, or additionally, a follicular diameter of a human follicle that is indicative of a mature or maturing follicle is a diameter between about 30 μm to 10,000 μm, between about 50 μm to 5000 μm, between about 100 μm to 2000 μm, between about 200 μm to 1000 μm, between about 300 μm to 900 μm, between about 400 μm to 800 μm, or between about 500 μm to 700 μm.

By way of example, but not by limitation, in some embodiments, an oocyte diameter of a human oocyte that is indicative of a mature or maturing oocyte is a diameter greater than about 10 μm. Alternatively, or additionally, a follicular diameter of a human follicle that is indicative of a mature or maturing oocyte is a diameter between about 10 μm to 200 μm, or between about 20 μm to 175 μm, or between about 30 μm to 150 μm, or between about 40 μm to 125 μm, or between about 50 μm to 100 μm, or between about 60 μm to 75 μm.

In some embodiments, an increase in granulosa cell number in ovarian tissue is measured by comparison of the number of granulosa cells in the ovarian tissue before contact with granulosa cells or granulosa cell precursors to the number of granulosa cells in the ovarian tissue after contact with granulosa cells or granulosa cell precursors. Alternatively, or additionally, an increase in granulosa cell number in ovarian tissue is measured by comparison of the number of granulosa cells in the ovarian tissue after contact with granulosa cells or granulosa cell precursors as compared to age-matched ovarian tissue not contacted with granulosa cells or granulosa cell precursors.

In some embodiments, the increase in granulosa cell number in ovarian tissue contacted with granulosa cells or granulosa cell precursors is measured as a percent increase of about 1%, 5%, 10%, 20%, 30%, 40%, 50%, 60%, 70%, 80%, 90%, 100% or a percent increase between any two of these values as compared to, e.g., ovarian tissue before contact with granulosa cells or granulosa cell precursors or age-matched ovarian tissue not contacted with granulosa cells or granulosa cell precursors.

Steroid hormones produced by the contacting of granulosa cells or granulosa cell precursors with ovarian tissue include, but are not limited to, estradiol, estriol, estrone, pregnenolone, and progesterone. In some embodiments, the increase in steroid hormones produced in ovarian tissue contacted with granulosa cells or granulosa cell precursors is measured as a percent increase of about 1%, 5%, 10%, 20%, 30%, 40%, 50%, 60%, 70%, 80%, 90%, 100% or a percent increase between any two of these values as compared to, e.g., ovarian tissue before contact with granulosa cells or granulosa cell precursors or age-matched ovarian tissue not contacted with granulosa cells or granulosa cell precursors.

Provided herein are also methods of increasing the fertilization rate of an oocyte, wherein the oocyte is in a granulosa cell-oocyte complex, the method comprising administering a compound to the granulosa cell, wherein the compound increases the mitochondrial membrane potential (MMP) of the granulosa cell.

Methods for the Preparation and Transfer of Mitochondria

Methods for the preparation and transfer of mitochondria are known in the art and can be carried out as previously described in the art, or using comparable techniques. See, for example, Perez et al., Cell Death and Differentiation 2007 3:524-33. Epub 2006 Oct. 13, and Perez et al., Nature 2000, 403:500-1, the contents each of which are incorporated herein by reference. Briefly, granulosa cells (GCs) can be isolated and cultured. In one method, 2 mL of mitochondrial lysis buffer (0.3 M sucrose, 1 mM EDTA, 5 mM MOPS, 5 mM KH2P04, 0.1% BSA) is added to each plate, and the cells are removed using a cell scraper. The cell suspension is transferred into a small glass tissue douncer and homogenized until smooth (approximately 10 up-and-down strokes), and the lysate is centrifuged at 600 g for 30 minutes at 4° C. The supernatant is removed and spun at 10,000 g for 12 minutes at 4° C., and the resulting crude mitochondrial pellet is resuspended in 0.2 mL of 0.25 M sucrose. This sample is then layered over a 25-60% Percoll density gradient diluted with 0.25 M sucrose and centrifuged at 40,000 g for 20 minutes at 17° C. The interface band is extracted from the gradient and washed in 2 volumes of 0.25 M sucrose before a final centrifugation at 14,000 g for 10 min at 4° C. to yield a mitochondrial pellet.

The mitochondrial pellet can also be prepared as described Frezza et al. Nature Protocols 2007 2:287-295, the contents of which are incorporated herein by reference. In specific embodiments of the invention, the total GC-derived mitochondrial population in a tissue, cell, lysed cell, or fraction thereof can be isolated, characterized and/or enumerated using a FACS-based method with a fluorescent probe that specifically binds to mitochondria in a mitochondrial membrane potential (MMP)-independent manner. Fluorescent probes that specifically bind to mitochondria in a MMP-independent manner include, but are not limited to, accumulation dependent probes (e.g., JC-1 (red spectrum; Invitrogen T3168, Life Technologies Corp., Carlsbad, CA), MitoTracker Deep Red FM (Invitrogen M22426, Life Technologies Corp., Carlsbad, CA) and JC-1 (green spectrum; Invitrogen T3168, Life Technologies Corp., Carlsbad, CA).

Functional (e.g., respiring) mitochondria can be sorted and collected, preferably with exclusion of residual unlysed cells and non-functional mitochondria, based on size and fluorescence intensity using mitochondrial tracking probes that indicate mitochondrial mass including, but not limited to, non-oxidation dependent probes (e.g., MitoTracker Green FM (Invitrogen M7514, Life Technologies Corp., Carlsbad, CA). Optionally, the FACS-based method can also be employed to selectively yield a substantially pure population of functional (e.g., respiring) mitochondria using a mitochondrial membrane fluorescent probe that specifically binds to mitochondria in a MMP-dependent manner.

Fluorescent probes that specifically bind to mitochondria in a MMP-dependent manner include, but are not limited to, reduced oxidative state mitotracker probes (e.g., MitoTracker Red CM-H2XRos (Invitrogen M7513, Life Technologies Corp., Carlsbad, CA) and MitoTracker Orange CM-H2TMRos (Invitrogen M7511, Life Technologies Corp., Carlsbad, CA). Furthermore, dual-labeling using MMP-dependent and MMP-independent probes can be conducted to quantitate the ratio of functional to total mitochondria in a tissue, cell, lysed cell or fraction derived therefrom. In specific embodiments, the ratio is greater than about 0.02, 0.025, 0.033, 0.04, 0.05, 0.1, or about 0.2. When using probes for differential screening based on MMP, spectral color is the major determining factor to designate functional mitochondria, and forward scatter can be used to distinguish the fluorescent mitochondria released from lysed cells from those still contained in residual unlysed cells.

Mitochondrial pellets can also be prepared as described by Taylor et al., Nat. Biotechnol. 2003 21(3): 239-40; Hanson et al., Electrophoresis. 2001 22(5): 950-9; and Hanson et al., J. Biol. Chem. 2001 276(19): 16296-301. In specific embodiments of the invention, the total GC-derived mitochondrial population in a tissue, cell, lysed cell, or fraction thereof can be isolated, characterized and/or enumerated using a differential centrifugation method.

Following isolation, assessment of mitochondrial function or mtDNA integrity (e.g., mutations and deletions) can be conducted according to methods known in the art (Duran et al., Fertility and Sterility 2011 96(2):384-388; Aral et al., Genetics and Molecular Biology 2010 33: 1-4; Chan et al., Molecular Human Reproduction 2005 1 1(12):843-846; Chen et al., BMC Medical Genetics 2011 12:8). Populations of mitochondria sorted according to functional parameters (e.g., MMP dependent/active or MMP-independently active plus inactive) or mitochondria from less preferred GC sources, including samples of limited size, can be now be obtained according to the methods of the invention. Mitochondrial compositions of the invention can generate, for example, about 1 pmol ATP per fg mtDNA to about 6 pmol ATP per fg mtDNA (e.g., about 1, 2, 3, 4, 5, or 6 pmol ATP per fg mtDNA). In specific embodiments, between about 1.0 pmol to 1.4 pmol ATP per fg mtDNA is generated within about 10 minutes to about 15 minutes.

The percentage of mutations in a population of mitochondria can be assessed by first determining the number of mitochondria present in a biological sample and next, determining the copy number of mitochondrial DNA present in the sample. Standard mutation analysis can be employed and compared to the number of mitochondria and copy number of mitochondrial DNA to calculate the percentage of mutations in the population of mitochondria. For example, compositions and methods of the invention can provide a population of mitochondria in which less than about 5% to about 25% (e.g., about 5%, 10%, 15%, 20% to about 25%) of the mitochondrial DNA comprises a deletion mutation within nucleotides 8470-13447 of the mitochondrial genome.

Optionally, one or more bioenergetic agents can be added to the mitochondrial preparation prior to mitochondrial extraction from cells, mitochondrial isolation from cell extracts or mitochondrial injection. The material to be injected (e.g., mitochondrial suspension) is transferred to a microinjection needle according to methods known in the art. Microinjection needles and holding pipettes can be made using a Sutter puller (Sutter Instruments, Novato, CA, USA) and a De Fonbrune Microforge (EB Sciences, East Granby, CT, USA). The microinjection needles have inner diameters of 5 μm with blunt tips. The material to be injected is aspirated into the needle by negative suction. Between about 1×lO3-to about 5×104 mitochondria from OSCs or their progeny can be injected (e.g., about 1, 2, 3, 4, 5, 6, 7, 8 to 9×103; about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 to about $5×10^4$ mitochondria). The mitochondrial suspension in sucrose (e.g., 5-7 pi containing approximately $1×10^3$-$5×10^4$ mitochondria from OSCs or their progeny) can be injected into oocytes using a Piezo micromanipulator. Oocytes that survive the microinjection procedure are transferred for culture and optionally, assessment or cryopreservation prior to in vitro fertilization or intrauterine insemination. Methods of oocyte cryopreservation are well known in the art. For details, see for example, Porcu et al., Molecular and Cellular Endocrinology 2000 169:33-37; Mandelbaum, Human Reproduction 2000 15:43-47; and Fabbri et al., Molecular and Cellular Endocrinology 2000 169:39-42, the contents of which are incorporated herein by reference.

ADDITIONAL EXEMPLARY EMBODIMENTS

In exemplary embodiment 1, provided herein is a method for detection of changes in GC mitochondrial function.

In exemplary embodiment 2, provided herein is the method of embodiment 1, wherein the changes detected in GC mitochondrial function occur before other known biological markers of ovarian aging in female subjects.

In exemplary embodiment 3, provided herein is the method of embodiment 1, wherein the changes detected in GC mitochondrial function can be used to identify female subjects at risk for pending ovarian aging.

In exemplary embodiment 4, provided herein is the method of embodiment 1, wherein the changes detected in GC mitochondrial function can be used to identify female subjects at risk for premature ovarian aging resulting from genetic disorders, disease conditions, and exposure to agents that can cause reproductive harm, among others.

In exemplary embodiment 5, provided herein is the method of embodiment 1, wherein the change detected in GC mitochondria is MMP.

In exemplary embodiment 6, provided herein is the method of embodiment 1, wherein the changes detected in GC mitochondrial function are analyzed in a human subject.

In exemplary embodiment 7, provided herein is a method for diagnostically identifying which individual GC-oocyte complexes, based on changes in GC mitochondrial function, are more or less likely to undergo successful fertilization.

In exemplary embodiment 8, provided herein is the method of embodiment 7, wherein the change in GC mitochondrial function used for predictive evaluation of oocyte fertilization potential is MMP.

In exemplary embodiment 9, provided herein is the method of embodiment 7, wherein GCs exhibiting a majority of mitochondria with a high MMP can be used to predict a greater chance of successful fertilization of the oocyte in contact with those GCs.

In exemplary embodiment 10, provided herein is the method of embodiment 7, wherein GCs exhibiting a majority of mitochondria with a low MMP can be used to predict a lesser chance of successful fertilization of the oocyte in contact with those GCs.

In exemplary embodiment 11, provided herein is the method of embodiment 7, wherein GCs exhibiting a majority of mitochondria with a high MMP can be used to predict a greater chance of successful preimplantation embryo development after fertilization of the oocyte in contact with those GCs.

In exemplary embodiment 12, provided herein is the method of embodiment 7, wherein GCs exhibiting a majority of mitochondria with a low MMP can be used to predict lesser chance of successful preimplantation embryo development after fertilization of the oocyte in contact with those GCs.

In exemplary embodiment 13, provided herein is the method of embodiment 7, wherein GCs exhibiting a majority of mitochondria with a high MMP potential can be used to predict a greater chance of pregnancy success after fertilization of the oocyte in contact with those GCs.

In exemplary embodiment 14, provided herein is the method of embodiment 7, wherein GCs exhibiting a majority of mitochondria with a low MMP potential can be used to predict a lesser chance of pregnancy success after fertilization of the oocyte in contact with those GCs.

In exemplary embodiment 15, provided herein is the method of embodiment 7, wherein the fertilization of the oocyte occurs in vivo.

In exemplary embodiment 16, provided herein is the method of embodiment 7, wherein the fertilization of the oocyte occurs in vitro.

In exemplary embodiment 17, provided herein is the method of embodiment 7, wherein the fertilization involves an oocyte from a human subject.

In exemplary embodiment 18, provided herein is a method of increasing the fertilization rates of an oocyte in a GC-oocyte complex by transferring a composition of mitochondria with a high MMP into the GCs of a GC-oocyte complex.

In exemplary embodiment 19, provided herein is the method of embodiment 18, wherein the composition comprising mitochondria is derived from cells autologous to the subject, In exemplary embodiment 20, provided herein is the method of embodiment 18, wherein the composition comprising mitochondria is derived from GCs.

In exemplary embodiment 21, provided herein is the method of embodiment 18, wherein the composition comprising mitochondria is derived from those GCs in direct physical contact with the oocyte, which may be referred to as cumulus-granulosa cells or cumulus-cells.

In exemplary embodiment 22, provided herein is the method of embodiment 18, wherein the composition comprising mitochondria is derived from stem or progenitor cells that can give rise to GCs, including, but not limited to embryonic stem cells, induced pluripotent stem cells, bone marrow-derived stem or progenitor cells, blood-derived stem or progenitor cells, mesenchymal stem cells, and germline stem or progenitor cells.

In exemplary embodiment 23, provided herein is the method of embodiment 18, wherein the composition comprising mitochondria is prepared using density gradient separation.

In exemplary embodiment 24, provided herein is the method of embodiment 18, wherein the composition comprising mitochondria is prepared using differential centrifugation.

In exemplary embodiment 25, provided herein is the method of embodiment 18, wherein the composition comprising mitochondria is prepared using flow cytometry.

In exemplary embodiment 26, provided herein is the method of embodiment 18, wherein the mitochondrial composition is comprised of at least 50% mitochondria with a high MMP, more preferably of at least 70% mitochondria with a high MMP, and most preferably of at least 90% mitochondria with a high MMP.

In exemplary embodiment 27, provided herein is the method of embodiment 18, wherein the transfer of the mitochondrial composition is by external exposure of the GC-oocyte complex to the mitochondrial composition.

In exemplary embodiment 28, provided herein is the method of embodiment 18, wherein the transfer of the mitochondrial composition is achieved by external exposure of the GC-oocyte complex to the mitochondrial composition in vivo.

In exemplary embodiment 29, provided herein is the method of embodiment 18, wherein the transfer of the mitochondrial composition is achieved by external exposure of the GC-oocyte complex to the mitochondrial composition in vitro.

In exemplary embodiment 30, provided herein is the method of embodiment 18, wherein the transfer of the mitochondrial composition is achieved by vesicle-mediated transfer of the mitochondrial composition into the GC-oocyte complex.

In exemplary embodiment 31, provided herein is the method of embodiment 18, wherein the transfer of the mitochondrial composition is achieved by vesicle-mediated transfer of the mitochondrial composition into the GC-oocyte complex in vivo.

In exemplary embodiment 32, provided herein is the method of embodiment 18, wherein the transfer of the mitochondrial composition is achieved by vesicle-mediated transfer of the mitochondrial composition into the GC-oocyte complex in vitro.

In exemplary embodiment 33, provided herein is the method of embodiment 18, wherein the mitochondrial composition contains at least 500 mitochondria, more preferably at least 2,500 mitochondria, and most preferably at least 5,000 mitochondria.

In exemplary embodiment 34, provided herein is the method of embodiment 18, wherein the oocyte in a GC-oocyte complex that receives a composition of mitochondria with a high MMP is from a human subject.

In exemplary embodiment 35, provided herein is a method for detection of changes detected in GC mitochondrial function that can be used to assess the efficacy or potential of a therapeutic compound or agent designed to increase or restore female fertile potential.

In exemplary embodiment 36, provided herein is the method of embodiment 35, wherein the changes detected in GC mitochondrial function occur before changes in other known biological markers of improved fertile potential in female subjects.

In exemplary embodiment 37, provided herein is the method of embodiment 35, wherein the changes detected in GC mitochondrial function can be used to assess the efficacy or potential of compounds or factors known to influence oocyte quality and/or female fertile potential, including, but not limited to, co-enzyme Q10 (CoQ10), ubiquinol, resveratrol, melatonin, growth hormone, omega fatty acids, antioxidants (e.g., vitamin-C, vitamin-E), NAD+, and nicotinamide mononucleotide (NMN).

In exemplary embodiment 38, provided herein is the method of embodiment 35, wherein the change detected in GC mitochondria is MMP.

In exemplary embodiment 39, provided herein is the method of embodiment 35, wherein the changes detected in GC mitochondrial function are analyzed in a human subject.

In exemplary embodiment 40, provided herein is a method for improving the ex-vivo generation of functional oocytes from stem or progenitor cells, involving exposure of stem or progenitor cells used for gametogenesis, or oocytes derived from stem or progenitor cells, to cells with mitochondria with a high MMP.

In exemplary embodiment 41, provided herein is the method of embodiment 40, wherein the stem or progenitor cells used for gametogenesis are derived from, but not limited to, embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 42, provided herein is the method of embodiment 40, wherein the cells containing mitochondria with a high MMP are autologous to the subject.

In exemplary embodiment 43, provided herein is the method of embodiment 40, wherein the cells containing mitochondria with a high MMP are derived from GCs.

In exemplary embodiment 44, provided herein is the method of embodiment 40, wherein the cells containing mitochondria with a high MMP are those GCs in direct physical contact with the oocyte, which may be referred to as cumulus-granulosa cells or cumulus-cells.

In exemplary embodiment 45, provided herein is the method of embodiment 40, wherein the cells containing mitochondria with a high MMP are stem or progenitor cells that can give rise to GCs, including, but not limited to embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 46, provided herein is the method of embodiment 40, wherein cells with a high MMP are brought in direct or indirect contact with an oocyte formed from cells used for gametogenesis, including, but not limited to, embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 47, provided herein is the method of embodiment 40, wherein the stem or progenitor cells used for gametogenesis to produce oocytes that are exposed to cells with mitochondria with a high MMP are from a human subject.

In exemplary embodiment 48, provided herein is a method for improving the ex-vivo generation of functional oocytes from stem or progenitor cells, involving exposure of stem or progenitor cells used for gametogenesis to mitochondria with a high MMP.

In exemplary embodiment 49, provided herein is the method of embodiment 48, wherein the stem or progenitor cells used for gametogenesis are derived from, but not limited to, embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 50, provided herein is the method of embodiment 48, wherein the cells from which mitochondria with a high MMP are derived are autologous to the subject.

In exemplary embodiment 51, provided herein is the method of embodiment 48, wherein the cells from which mitochondria with a high MMP are derived are GCs.

In exemplary embodiment 52, provided herein is the method of embodiment 48, wherein the cells from which mitochondria with a high MMP are derived are those GCs in direct physical contact with the oocyte, which may be referred to as cumulus-granulosa cells or cumulus-cells.

In exemplary embodiment 53, provided herein is the method of embodiment 48, wherein the cells from which mitochondria with a high MMP are derived are stem or progenitor cells that can give rise to GCs, including, but not limited to embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 54, provided herein is the method of embodiment 48, wherein mitochondria with a high MMP are brought in direct contact with a GC-oocyte complex formed from cells used for gametogenesis, including, but not limited to, embryonic stem cells, induced pluripotent stem cells, bone marrow-derived stem or progenitor cells, blood-derived stem or progenitor cells, mesenchymal stem or progenitor cells, and germline stem or progenitor cells.

In exemplary embodiment 55, provided herein is the method of embodiment 48, wherein the stem or progenitor cells used for gametogenesis to produce GC-oocyte complexes that are exposed to mitochondria with a high MMP are from a human subject.

EXAMPLES

The invention now being generally described, it will be more readily understood by reference to the following examples which are included merely for purposes of illustration of certain aspects and embodiments of the present invention, and are not intended to limit the invention.

Example 1. Methods

Mitochondrial Isolation, Transplantation and Imaging

Cells are grown followed by harvesting and mitochondrial isolation utilizing a Mitochondrial Isolation Kit for Cultured Cells (Thermo Scientific) paired with Dounce homogenization. Directly following isolation, mitochondria were resuspended in 500 μL of respiration buffer (250 mM sucrose, 20 mM HEPES, 0.5 mM EGTA [pH 8.0]) and centrifuged for 5 minutes at 12,000×g at 4° C. [Moskowitzova et al. 2018]. The samples were then resuspended in 50 μL of respiration buffer and added to recipient cells cultured in 12-well plates for co-culture transplantation. Co-culture incubations were performed overnight at 37° C. in a 5% $CO_2$ incubator. Mitochondrial quantity for comparative experiments was estimated using a BCA assay (Thermo Scientific). For fluorescent transplantation, isolated mitochondria were immediately labeled with 100 nM Mitotracker Red CMXROS (Invitrogen) for 15 minutes on ice, and washed with respiration buffer twice. On the last wash, the supernatant from the stained mitochondria was collected and added to MRC-5 cells in parallel as a negative control. Fluorescent images were collected with Zeiss microscope.

The mitochondria may be prepared by density gradient separation as described in Graham, J. M., *Curr Protoc Cell Biol.* 2001 May; Chapter 3: Unit 3.4.

The mitochondria may be prepared by density gradient separation as described in Graham, J. M., *Curr Protoc Cell Biol.* 2001 May; Chapter 3: Unit 3.3.

The mitochondria may be prepared by flow cytometry as described in Example 2.

COX-IV Staining for Flow Cytometry Analysis

Cells cultured in 12-well plates were washed with PBS, harvested, fixed and permeabilized according to Abcam guidelines. Briefly, samples were washed in excess PBS twice, and resuspended in 100 μL of 1:1600 diluted rabbit anti-human COX-IV primary antibody (Abcam), prepared in 5% BSA (Cell signaling technology) in PBS. Samples were then incubated for 1 hour at room temperature. Post-primary antibody labeling, samples were incubated with 100 μL of 1:50 Goat anti-Rabbit IgG (H+L) Secondary Antibody, DyLight 650 (Invitrogen) for 30 minutes at room temperature, protected from light. Finally, samples were washed with Antibody Dilution Buffer twice, resuspended in 250 μL PBS and filtered through 100 μm filter into FACS tubes. Samples were interrogated with FCS, SSC, and APC lasers on an FACSAria II Flow Cytometer (BD Biosciences) on the DIVA (version 8.0.1) platform and the data collected was further analyzed using FlowJo (version 10.7.1).

Example 2. Sorting Mitochondria

Figure 1B:
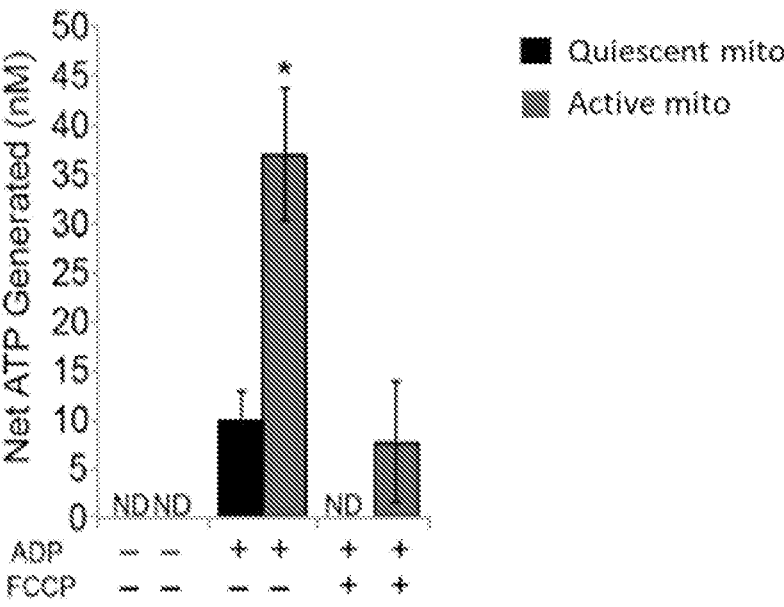

Using a flow cytometry platform that enables nano-scale sorting, numerous properties of mitochondria in cells can be assessed, including size and membrane potential (MMP or $\Delta\psi m$). The flow cytometry platform is described in MacDonlad J. A., et al. *Commun Biol.* 2019 Jul. 11; 2:258. Here we show that mitochondria can be isolated based on size (small versus large, FIG. 1A), and that size and $\Delta\psi m$ are positively associated (FIG. 1B). Mitochondria isolated by fluorescence-activated mitochondrial sorting (FAMS) retain full functional capacity to generate ATP from ADP substrate (FIG. 1B; small mitochondria exhibit low $\Delta\psi m$; large mitochondria exhibit high $\Delta\psi m$).

A freeze-fracture method was used for scanning electron microscopy (SEM) specifically for use on mitochondrial isolates. The freeze-fracture method is described in MacDonlad J. A., et al. *Micron.* 2017 October; 101:25-31. The freeze-fracture method is also described in MacDonlad J. A., et al. *MethodsX.* 2018 May 19; 5:593-598. Mitochondria isolated by FAMS retain normal ultrastructural features (FIG. 2).

Example 3. Mitochondrial Membrane Potential Dissipates in GCs with Age

For this analysis, GC-oocyte complexes were collected from mice at 1.5, 7, and 12 months of age (representing young adult, mid-reproductive life, and reproductively aged mice). Mitochondria from GCs and oocytes were labeled using $\Delta\Psi m$ (MMP)-dependent dyes and analyzed separately by flow cytometry. While $\Delta\Psi m$ is relatively unchanged in oocytes with age, GCs exhibit dissipated $\Delta\Psi m$ by 7-months that worsens much further by 12 months of age (FIG. 3), when oocyte quality has severely deteriorated and the females exhibit fertility issues due to maternal aging.

Example 4. Mitochondrial Transfer (Transplantation)

Mitochondria isolated from donor cells are cultured with recipient cells, resulting in rapid uptake (by 4 hours) through a mechanism involving actin-mediated endocytosis and micropinocytosis (FIG. 4).

The mitochondria may also be transferred via vesicle-mediated transfer as described in Torralba T, et al. *Front. Cell Dev. Biol.*, 28 Sep. 2016.

Example of mitochondrial transfer into recipient cells. Donor cell mitochondria were labeled with MitoTracker-Red to facilitate mitochondrial tracking (red fluorescence), and the mitochondria were then incubated with, and incorporated into recipient, cells within 4 hours. Prior to transfer, the mitochondrial pellet was rinsed post-staining with MitoTracker-Red, and the wash was added to control cells to rule out artifactual uptake of dye by recipient mitochondria.

Figure 5A:
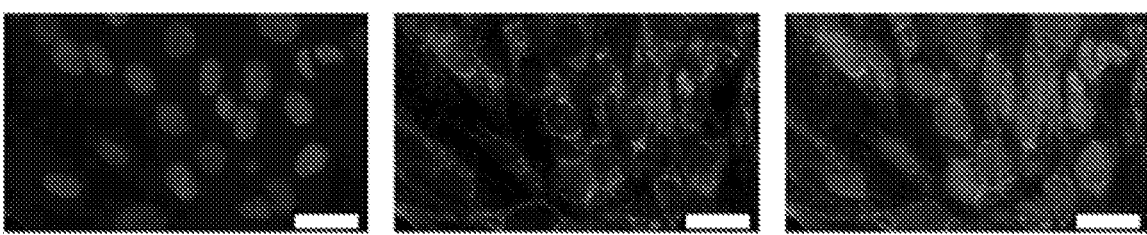
FIGS. 5A-5G show mitochondrial transfer (transplantation) methodology.
Figure 5B:

We confirmed exogenous mitochondrial internalization into recipient cells by labeling the isolated mitochondria with MitoTracker Red CMXROS before introducing them into co-culture. Our results demonstrate successful internalization of fluorescent mitochondria into recipient cells and a conclusive lack of reagent leakage exhibited by our control group (FIGS. 5A-5B).

Figure 5C:
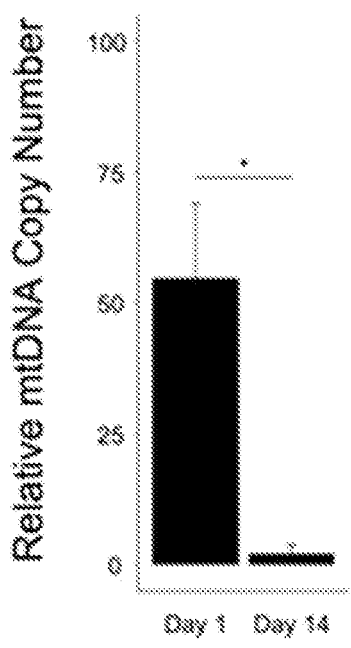

For the transplantation of exogenous mitochondria into our depleted cell-line, we were able to use the highly-sensitive approach of qPCR, a standard assay commonly utilized in this genre of experiments [Kim et al. 2018, Kitani et al. 2014]. As recipient cells contain no mtDNA, the presence of exogenous mitochondria increased this value drastically. While our preliminary data indicated a prevalent increase in mtDNA upon mitochondrial transplantation, we set out to determine whether the exogenous mtDNA provided by the donor cells remained present in the recipient cell line on a long-term basis (14 days). Thus, recipient cells were transplanted with donor mitochondria overnight and cultured in parallel to other recipient cells which received a vehicle control. The following day, half of each sample was collected for mtDNA analysis, while the other half was re-introduced into cell culture. Two weeks after the transplant, cells were again collected for mtDNA qPCR and the two time-points were compared. The presence of these exogenous mitochondria is not maintained, as depicted by their absence 14 days succeeding co-culture (FIG. 5C).

Figure 5D:
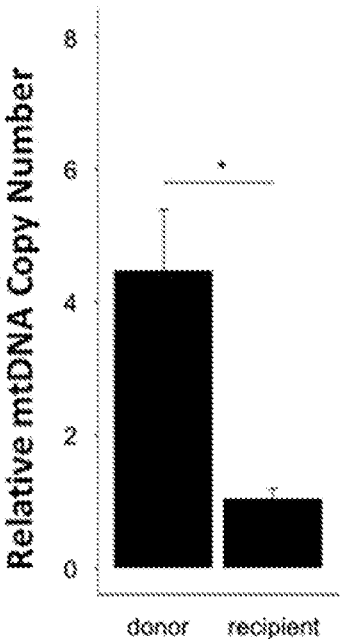
Figure 5E:
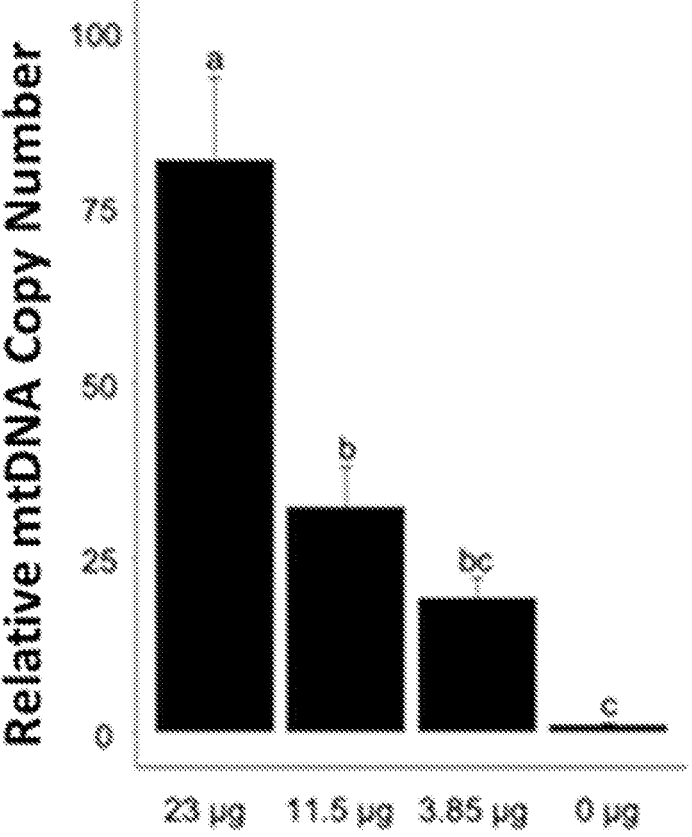
Figure 5F:
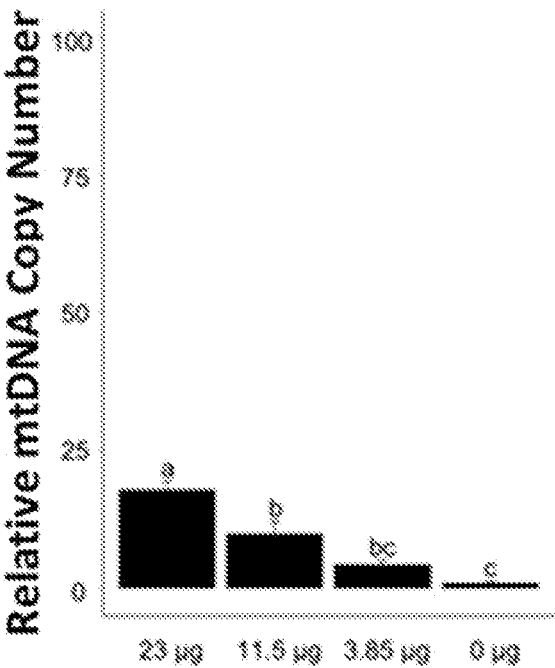
Figure 5G:
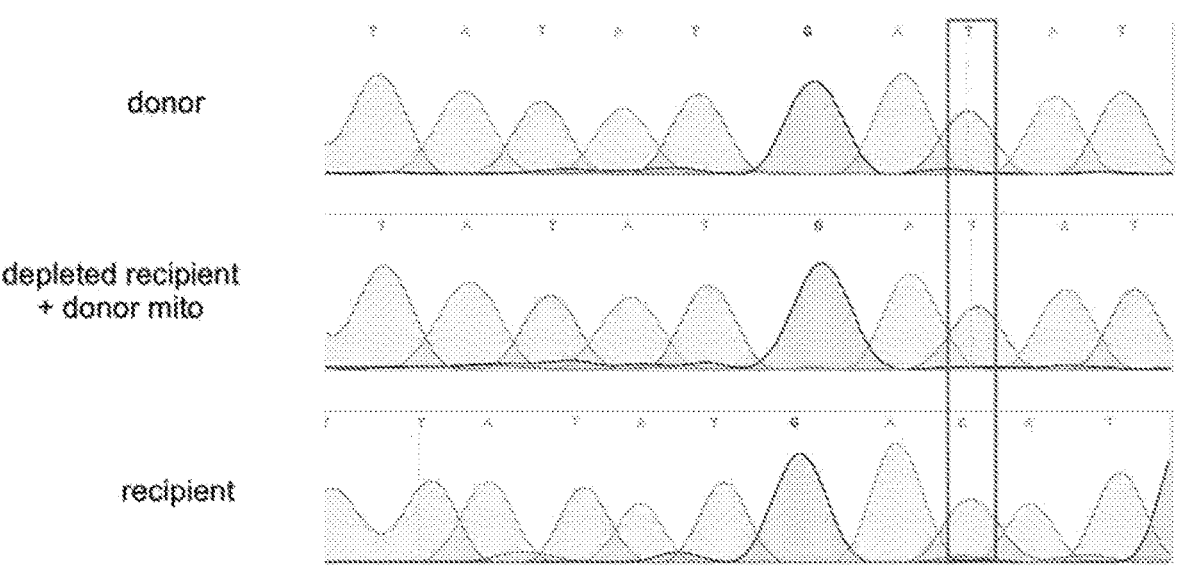

We further pursued another experiment to compare the internalization of exogenous mitochondria (from donor cells) against endogenous mitochondria (from recipient cells). Recipient cells served as an excellent model for this because there is no possibility of mitochondrial fusion leading to the harboring of exogenous mtDNA by endogenous mitochondria. In order to test this, we performed mitochondrial transplants utilizing both exogenous mitochondria derived from donor cells as well as endogenous mitochondria derived from recipient cells. To ensure equivalent quantities of isolated mitochondria were introduced to the co-culture, we ran a BCA assay to determine approximate concentrations of mitochondrial material and used 4 different, parallel quantities. We conclusively determined that there is no preference for internalization of exogenous versus endogenous mitochondria as established by the relative mitochondrial quantity provided by each cell line and the internalization observed (FIGS. 5D-5F). Finally, to ensure the mtDNA present in recipient cells transplanted with donor mitochondria belonged to the donor line, a section of mtDNA was sequenced to differentiate the endogenous and exogenous mtDNA by a single-nucleotide polymorphism (SNP) and match it to the mtDNA present in the transplanted group (FIG. 5G).

Figure 6A:
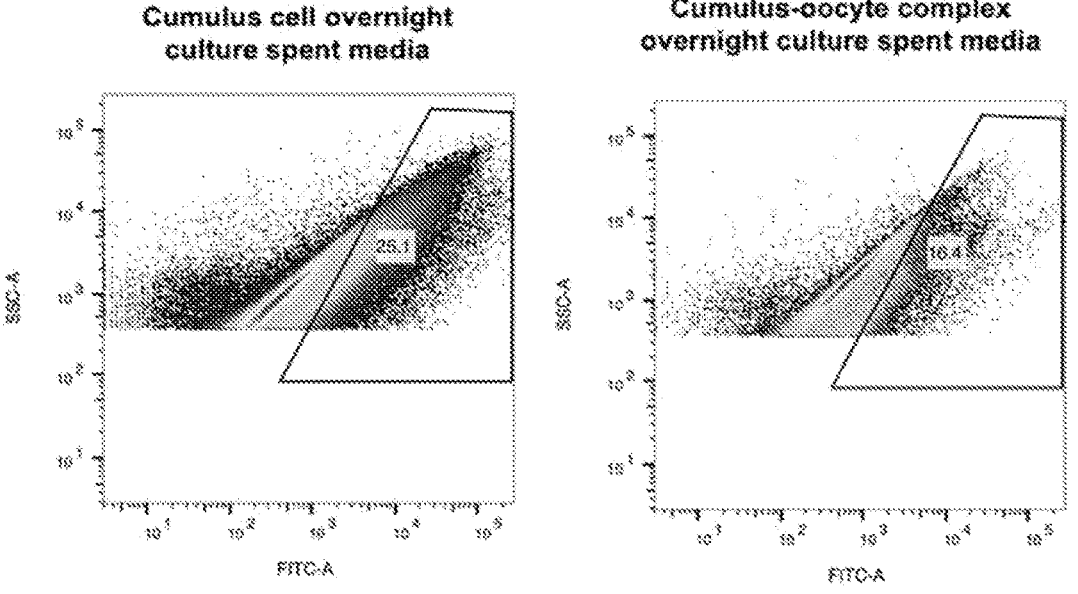
FIGS. 6A-6C show cumulus granulosa cells release mitochondria into cell culture media during overnight culture post-collection.
Figure 6B:
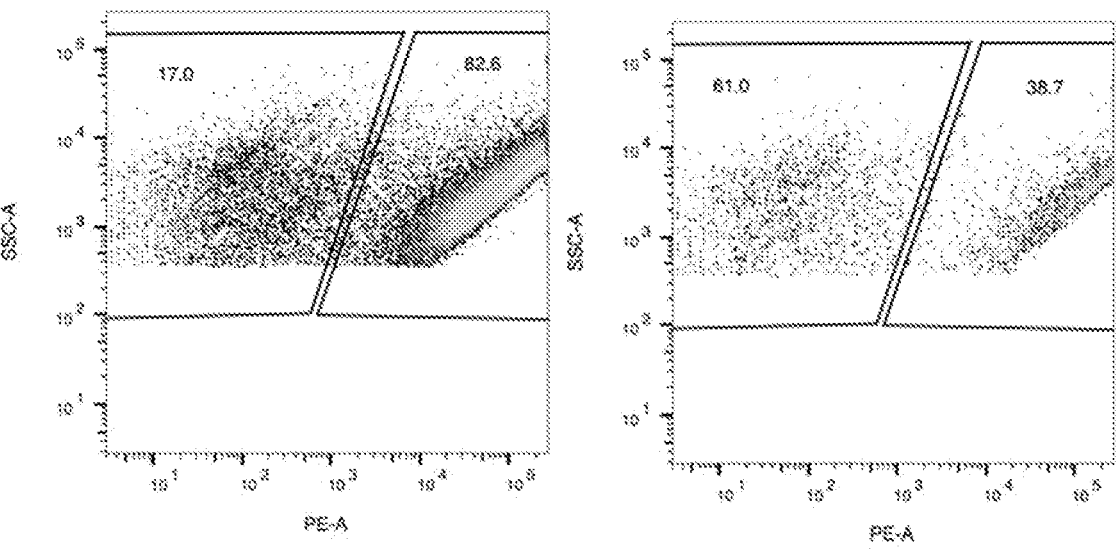
Figure 6C:
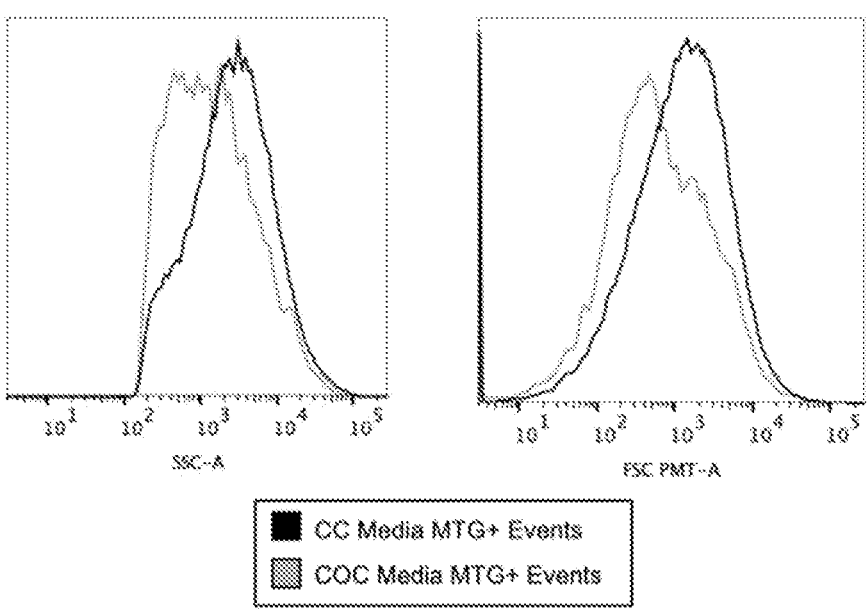

Example 5. Cumulus Granulosa Cells Release Mitochondria into Cell Culture Media During Overnight Culture Post-Collection Cumulus cells were detached from metaphase II (MII) oocytes using hyaluronidase, and they were then cultured overnight in DMEM/F12 base medium supplemented with 4 mg/mL BSA and 1% penicillin-streptomycin. In parallel, intact cumulus-granulosa complexes were cultured overnight in the same medium; both at 37° C., 5% $CO_2$. Fluorescence-activated mitochondrial sorting (FAMS) was then conducted using only the spent media from each of these cultures. 25.1% of events within the pre-determined size gate (0.22-2 μm) in the cumulus cell overnight culture media sample displayed positive fluorescence for MitoTracker Green FM, while only 16.4% of events within the same size gate displayed positive fluorescence in the cumulus-oocyte complex overnight culture spent media sample (FIG. 6A). JC-1 aggregate fluorescence, measured in the PE-A channel via FAMS (MacDonald et al., *Communications Biology* 2019 Jul. 11; 2:258), is indicative of high-mitochondrial membrane potential; which is classically used as a measure of mitochondrial respiratory activity (FIG. 6B). Cumulus granulosa cell mitochondria obtained from culture media can be stratified based on size, as determined by side scatter (SSC) and forward scatter (FSC) (FIG. 6C).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of increasing the fertilization rate of an oocyte, wherein the oocyte is in a granulosa cell-oocyte complex, the method comprising transferring a composition of mitochondria into the granulosa cells, wherein the transferred mitochondria have a higher mitochondrial membrane potential (MMP) than the mitochondria in the granulosa cells.

2. The method of claim 1, wherein the transferred mitochondria are derived from an autologous or allogeneic cell.

3. The method of claim 2, wherein the autologous or allogeneic cell is a granulosa cell.

4. The method of claim 2, wherein the autologous or allogeneic cell is a cumulus cell.

5. The method of claim 2, wherein the transferred mitochondria are transferred by incubating the autologous or allogeneic cell with the granulosa cell-oocyte complex.

6. The method of claim 1, wherein the transferred mitochondria are derived from a stem cell or a progenitor cell.

7. The method of claim 6, wherein the stem cell or the progenitor cell is an embryonic stem cell, induced pluripotent stem cell, bone marrow-derived stem or progenitor cell, blood-derived stem or progenitor cell, mesenchymal stem cell, or germline stem or progenitor cell.

8. The method of claim 1, wherein the transferred mitochondria are prepared using density gradient separation.

9. The method of claim 1, wherein the transferred mitochondria are prepared using differential centrifugation.

10. The method of claim 1, wherein the transferred mitochondria are prepared using flow cytometry.

11. The method of claim 1, wherein the composition of mitochondria comprises at least 50%, at least 70%, or at least 90% mitochondria with higher mitochondrial membrane potential (MMP) than the mitochondria in the granulosa cells.

12. The method of claim 1, wherein the transferred mitochondria are transferred ex vivo.

13. The method of claim 1, wherein the transferred mitochondria are transferred in vivo.

14. The method of claim 1, wherein the transferred mitochondria are transferred in vitro.

15. The method of claim 1, wherein the transferred mitochondria are transferred by vesicle-mediated transfer.

16. The method of claim 1, wherein the composition of mitochondria comprises at least 500 mitochondria, at least 2,500 mitochondria, or at least 5,000 mitochondria.

17. The method of claim 1, wherein the oocyte is from a human subject.

18. A method of in vitro fertilization, the method comprising incubating a composition of mitochondria with granulosa cells, wherein the granulosa cells are in a granulosa cell-oocyte complex; and fertilizing the oocyte in vitro to form a zygote, wherein the incubated mitochondria have a higher mitochondrial membrane potential (MMP) than the mitochondria in the granulosa cells.

19. The method of claim 18, wherein the incubated mitochondria are derived from an autologous or allogeneic cell.

* * * * *